US012758642B2

(12) United States Patent
Chung et al.

(10) Patent No.: US 12,758,642 B2
(45) Date of Patent: Oct. 13, 2026

(54) PEPTIDE EXHIBITING BOTULINUM TOXIN-LIKE ACTIVITY, AND USE THEREOF

(71) Applicant: CAREGEN CO, LTD., Anyang-si (KR)

(72) Inventors: Yong Ji Chung, Anyang-si (KR); Eun Mi Kim, Anyang-si (KR); Eung Ji Lee, Anyang-si (KR); Young Min Lee, Anyang-si (KR); Han A Kang, Anyang-si (KR)

(73) Assignee: CAREGEN CO, LTD., Anyang-si (KR)

( * ) Notice: Subject to any disclaimer, the term of this patent is extended or adjusted under 35 U.S.C. 154(b) by 807 days.

(21) Appl. No.: 18/009,388

(22) PCT Filed: Jun. 11, 2021

(86) PCT No.: PCT/KR2021/007326
§ 371 (c)(1),
(2) Date: Dec. 9, 2022

(87) PCT Pub. No.: WO2021/251791
PCT Pub. Date: Dec. 16, 2021

(65) Prior Publication Data

US 2024/0285780 A1 Aug. 29, 2024

(30) Foreign Application Priority Data

Jun. 12, 2020 (KR) ........................ 10-2020-0071661

(51) Int. Cl.

| | |
|---|---|
| ***A61K 47/64*** | (2017.01) |
| ***A61K 8/49*** | (2006.01) |
| ***A61K 8/64*** | (2006.01) |
| ***A61K 31/353*** | (2006.01) |
| ***A61K 47/55*** | (2017.01) |
| ***A61P 21/02*** | (2006.01) |
| ***A61Q 19/08*** | (2006.01) |
| ***C07K 7/06*** | (2006.01) |
| *A61K 38/00* | (2006.01) |

(52) U.S. Cl.
CPC ............ *A61K 47/551* (2017.08); *A61K 8/498* (2013.01); *A61K 8/64* (2013.01); *A61K 31/353* (2013.01); *A61K 47/64* (2017.08); *A61P 21/02* (2018.01); *A61Q 19/08* (2013.01); *C07K 7/06* (2013.01); *A61K 38/00* (2013.01); *A61K 2800/57* (2013.01)

(58) Field of Classification Search
None
See application file for complete search history.

(56) References Cited

U.S. PATENT DOCUMENTS

| | | | |
|---|---|---|---|
| 2009/0226387 | A1 | 9/2009 | Fasel et al. |
| 2013/0323187 | A1 | 12/2013 | Fasel et al. |
| 2015/0140046 | A1 | 5/2015 | Ferrer Montiel et al. |
| 2016/0279193 | A1 | 9/2016 | Otterlei |
| 2016/0289272 | A1 | 10/2016 | Otterlei et al. |
| 2017/0246266 | A1 | 8/2017 | Lee et al. |
| 2017/0267721 | A1 | 9/2017 | Chung et al. |
| 2018/0311333 | A1 | 11/2018 | Ruegg et al. |
| 2019/0040100 | A1 | 2/2019 | Chung et al. |
| 2019/0093095 | A1 | 3/2019 | Lee et al. |
| 2020/0197285 | A1 | 6/2020 | Chung et al. |
| 2020/0323953 | A1 | 10/2020 | Otterlei |
| 2021/0369585 | A1 | 12/2021 | Chung et al. |
| 2022/0062400 | A1 | 3/2022 | Ruegg et al. |
| 2023/0218498 | A1 | 7/2023 | Chung et al. |
| 2023/0285263 | A1 | 9/2023 | Chung et al. |
| 2023/0285264 | A1 | 9/2023 | Chung et al. |

FOREIGN PATENT DOCUMENTS

| | | | | |
|---|---|---|---|---|
| CA | 2895743 | A1 | 12/2016 | |
| CN | 102408470 | A | 4/2012 | |
| CN | 106459155 | A | 2/2017 | |
| CN | 107001420 | A | 8/2017 | |
| CN | 111148751 | A | 5/2020 | |
| EP | 4166155 | A1 | 4/2023 | |
| EP | 4166564 | A1 * | 4/2023 | ........... A61K 47/551 |
| JP | 2015-514721 | A | 5/2015 | |
| JP | 2017-527300 | A | 9/2017 | |
| JP | 2018-525971 | A | 9/2018 | |
| JP | 2018-531984 | A | 11/2018 | |
| KR | 20030087446 | A | 11/2003 | |
| KR | 20180028748 | A | 3/2018 | |
| WO | 2015067712 | A1 | 5/2015 | |

OTHER PUBLICATIONS

Office Action issued on Jun. 20, 2025 for the corresponding Chinese patent application Application No. 202180042048.7 (16 pgs including English Translation).
International Search Report and Written Opinion of the International Searching Authority for International Patent Application No. PCT/KR2021/007326 mailed Sep. 9, 2021 (11 pages).
GENBANK: BAP25669.1, "hypothetical protein (plasmid)[Clostridium botulinum]", (Jun. 12, 2015), (2 pages).
Arai et al., "Design, synthesis, and evaluation of Trolox-conjugated amyloid-b C-terminal peptides for therapeutic intervention in an in vitro model of Alzheimer's disease", Bioorganic & Medicinal Chemistry, 2016, 24:4138-4143, (6 pages).
Extended European Search Report issued on Nov. 8, 2023 for the corresponding European patent application No. 21822086.1 (10 pages).

(Continued)

*Primary Examiner* — Noble E Jarrell
(74) *Attorney, Agent, or Firm* — Merchant & Gould P.C.

(57) ABSTRACT

The present invention relates to a trolox-peptide conjugate which exhibits activity that relieves muscle contraction and increases the extracellular matrix, and which can be used as an active ingredient of a drug, a quasi-drug or a cosmetic product for muscle relaxation, neuromuscular disorder prevention or treatment, or the improvement of skin conditions including skin wrinkles.

7 Claims, 4 Drawing Sheets

Specification includes a Sequence Listing.

(56) References Cited

OTHER PUBLICATIONS

Murillo Divina, "et. al.", "Trolox reduces the effect of ethanol on acetylcholine-induced contractions and oxidative stress in the isolated rabbit duodenum", Jan. 1, 2011, vol. 103, No. 8, pp. 396-401.
Hong et. al., "The Effects of BMP2-related Peptide(OP10) on Dermal Wound Healing Using Trolox Conjugated Peptides Modified by Bone Morphogenic Protein-2", Tissue Engineering Part A, Dec. 14, 2016, vol. 22, No. 1, pp. S1-S156. (*Abstract 311; p. S82).
Hong Yoonjung et. al., "The Effects on Dermal Wound Healing Using Novel Peptide Modified by Bone Morphogenic Protein-2", Tissue Engineering and Regenerative Medicine, Aug. 1, 2014, vol. 11, No. 5, , pp. 397-404.
First Office Action issued on Dec. 12, 2023 for the corresponding Japanese patent application No. 2022-575915 (3 pages).
Karima A. El-Shamy et al., "The Effect of Both Vitamin E and Thymoquinone on Monoamine Neurotransmitter Changes Induced by Nicotine Treatment and Withdrawal in the Cortex and Hippocampus of Rat Brain", Journal of Applied Sciences Research , 2013, vol. 9, No. 6, pp. 4030-4040.
Office Action issued on May 11, 2026 for the corresponding Indian patent application Application No. 202217071651) (11 pgs including English Translation).

* cited by examiner

SEQUENCE LISTING

<160> NUMBER OF SEQ ID NOS: 9

<210> SEQ ID NO 1
<211> LENGTH: 5
<212> TYPE: PRT
<213> ORGANISM: Artificial Sequence
<220> FEATURE:
<223> OTHER INFORMATION: Peptide

<400> SEQUENCE: 1

Lys Phe Leu Ile Lys
1 5

<210> SEQ ID NO 2
<211> LENGTH: 20
<212> TYPE: DNA
<213> ORGANISM: Artificial Sequence
<220> FEATURE:
<223> OTHER INFORMATION: Forward primer for Col1a1

<400> SEQUENCE: 2
caccctcaag agcctgagtc 20

<210> SEQ ID NO 3
<211> LENGTH: 20
<212> TYPE: DNA
<213> ORGANISM: Artificial Sequence
<220> FEATURE:
<223> OTHER INFORMATION: Reverse primer for Col1a1

-continued

<400> SEQUENCE: 3
agacggctga gtagggaaca 20

<210> SEQ ID NO 4
<211> LENGTH: 20
<212> TYPE: DNA
<213> ORGANISM: Artificial Sequence
<220> FEATURE:
<223> OTHER INFORMATION: Forward primer for Fibronectin

<400> SEQUENCE: 4
ccaggaaccg agtacaccat 20

<210> SEQ ID NO 5
<211> LENGTH: 20
<212> TYPE: DNA
<213> ORGANISM: Artificial Sequence
<220> FEATURE:
<223> OTHER INFORMATION: Reverse primer for Fibronectin

<400> SEQUENCE: 5
atacccaggt tgggtgatga 20

<210> SEQ ID NO 6
<211> LENGTH: 20
<212> TYPE: DNA
<213> ORGANISM: Artificial Sequence
<220> FEATURE:
<223> OTHER INFORMATION: Forward primer for Elastin

<400> SEQUENCE: 6
ggacccctga ctcgcgacct 20

<210> SEQ ID NO 7
<211> LENGTH: 20
<212> TYPE: DNA
<213> ORGANISM: Artificial Sequence
<220> FEATURE:
<223> OTHER INFORMATION: Reverse primer for Elastin

<400> SEQUENCE: 7
ggggaggtgg gactgcccaa 20

<210> SEQ ID NO 8
<211> LENGTH: 25
<212> TYPE: DNA
<213> ORGANISM: Artificial Sequence
<220> FEATURE:
<223> OTHER INFORMATION: Forward primer for GAPDH

<400> SEQUENCE: 8
ggtgtgaacg gatttggccg tattg 25

<210> SEQ ID NO 9
<211> LENGTH: 25
<212> TYPE: DNA
<213> ORGANISM: Artificial Sequence
<220> FEATURE:
<223> OTHER INFORMATION: Reverse primer for GAPDH

<400> SEQUENCE: 9
ccgttgaatt tgccgtgagt ggagt 25

PEPTIDE EXHIBITING BOTULINUM TOXIN-LIKE ACTIVITY, AND USE THEREOF

CROSS-REFERENCE TO RELATED APPLICATIONS

This application is a National Stage Application of PCT/KR2021/007326, filed 11 Jun. 2021, which claims benefit of Serial No. 10-2020-0071661, filed 12 Jun. 2020 in Republic of Korea and which applications are incorporated herein by reference. To the extent appropriate, a claim of priority is made to each of the above disclosed applications.

SEQUENCE STATEMENT

This application contains a Sequence Listing, which has been submitted electronically in ASCII format and is hereby incorporated by reference in its entirety. Said ASCII copy, is named Sequence-Listing-09983-0260FPWO, was created on May 13, 2023, and is 2193 bytes in size.

TECHNICAL FIELD

The present invention relates to a trolox-peptide conjugate having a structure in which trolox and a peptide are chemically conjugated and a use thereof.

BACKGROUND ART

In order to regulate muscle relaxation and contraction, there is a neuromuscular junction in the upper layer of the muscle, and synaptic vesicles are loaded at the nerve terminal. Muscles contract by receiving a message from neurotransmitters transmitted inside a kind of nerve vesicle. When the neurotransmitters are to be released, a receptor complex called a soluble methylmaleimide-sensitive factor attachment protein receptor (SNAP receptor; SNARE) needs to be present, which allows the neurotransmitters to be docked with the muscles. If the SNARE receptor complex is slightly unstable, a carrier cannot actively release the neurotransmitters, and as a result, impulses generated at the neuromuscular synapse are not transmitted to the muscle, and the impulses are stopped, so that the muscle relaxes. In other words, less muscle contraction occurs, which means that the formation of wrinkles is reduced.

Meanwhile, a cause or a mechanism of the formation of facial expression wrinkles is caused by the tension of the epidermal muscle that pulls the skin inward. Such muscle tension is a result of facial muscle weakness and nerve hyperactivity. The nerve hyperactivity is an uncontrolled characteristic of excess release of neurotransmitters that stimulate muscle fibers. To this end, molecules that control the release of the neurotransmitters relax the muscle tension to contribute to removing facial wrinkles.

Based on this mechanism, many materials for inhibiting the formation of wrinkles have been studied and marketed.

Botulinum neurotoxin (BoNT) is a protease that cleaves a SNARE protein, a key protein involved in release of neurotransmitters, and is most commonly used in clinical trials and beauty for facial wrinkle removal. The BoNT cleaves the SNARE protein to inhibit the release of the neurotransmitters and block neurotransmission, resulting in paralysis of muscle cells penetrated with the BoNT.

However, since the paralytic effect of the BoNT is reversible for an average of 6 months, repeated injections of the BoNT are required, and an immune response to drugs may be caused due to sizes that may be recognized by a patient's immune system. The formation of antibodies to the BoNT causes significant loss of therapeutic efficacy, which is a serious problem.

Therefore, there is a need to develop a novel active ingredient having an effect of treating muscle spasms by regulating the release of neurotransmitters and reducing or removing facial asymmetry and/or facial wrinkles (especially, facial expression wrinkles) while having a simpler and more stable molecular structure without causing the immune response.

DISCLOSURE

Technical Problem

An object of the present invention is to provide a trolox-peptide conjugate in which a novel peptide and trolox are conjugated to inhibit the release of a neurotransmitter.

Another object of the present invention is to provide a composition for relieving muscle contraction or relaxing muscles.

Another object of the present invention is to provide a method for muscle relaxation.

Yet another object of the present invention is to provide a trolox-peptide conjugate used for muscle relaxation.

Yet another object of the present invention is to provide a pharmaceutical composition for preventing or treating neuromuscular disorder.

Yet another object of the present invention is to provide a method for preventing or treating neuromuscular disorder.

Yet another object of the present invention is to provide a trolox-peptide conjugate used for preventing or treating neuromuscular disorder.

Yet another object of the present invention is to provide a composition for improving skin conditions including wrinkle improvement.

Yet another object of the present invention is to provide a method for improving skin conditions.

Yet another object of the present invention is to provide a trolox-peptide conjugate used for improving skin conditions.

Technical Solution

An aspect of the present invention provides a trolox-peptide conjugate in which a peptide having an amino acid sequence of SEQ ID NO: 1 and trolox are conjugated.

Another aspect of the present invention provides a composition for muscle relaxation including the trolox-peptide conjugate as an active ingredient.

Further, the present invention provides a method for muscle relaxation including administering, to a subject, a trolox-peptide conjugate in which a peptide having an amino acid sequence of SEQ ID NO: 1 and trolox are conjugated.

Further, the present invention provides a trolox-peptide conjugate in which a peptide having an amino acid sequence of SEQ ID NO: 1 and trolox are conjugated, used for muscle relaxation.

Yet another aspect of the present invention provides a pharmaceutical composition for preventing or treating neuromuscular disorder including the trolox-peptide conjugate as an active ingredient.

Further, the present invention provides a method for preventing or treating neuromuscular disorder including administering, to a subject, a trolox-peptide conjugate in which a peptide having an amino acid sequence of SEQ ID NO: 1 and trolox are conjugated.

Further, the present invention provides a trolox-peptide conjugate in which a peptide having an amino acid sequence of SEQ ID NO: 1 and trolox are conjugated, used for preventing or treating neuromuscular disorder.

Yet another aspect of the present invention provides a composition for improving skin conditions including the trolox-peptide conjugate as an active ingredient.

Further, the present invention provides a method for improving skin conditions including administering, to a subject, a trolox-peptide conjugate in which a peptide having an amino acid sequence of SEQ ID NO: 1 and trolox are conjugated.

Further, the present invention provides a trolox-peptide conjugate in which a peptide having an amino acid sequence of SEQ ID NO: 1 and trolox are conjugated, used for improving skin conditions.

Advantageous Effects

According to the present invention, the trolox-peptide conjugate is useful as a regulator of intracellular responses involved with a SNARE and a neurotransmitter by inhibiting the release of the neurotransmitter. Therefore, the trolox-peptide conjugate of the present invention can be used as a composition for muscle relaxation, a composition for preventing or treating neuromuscular disorders, or a composition for improving skin conditions including wrinkle improvement.

However, the effects of the present invention are not limited to the above-mentioned effects, and other effects not mentioned will be clearly understood by those skilled in the art from the following description.

BEST MODE

Figure 1:
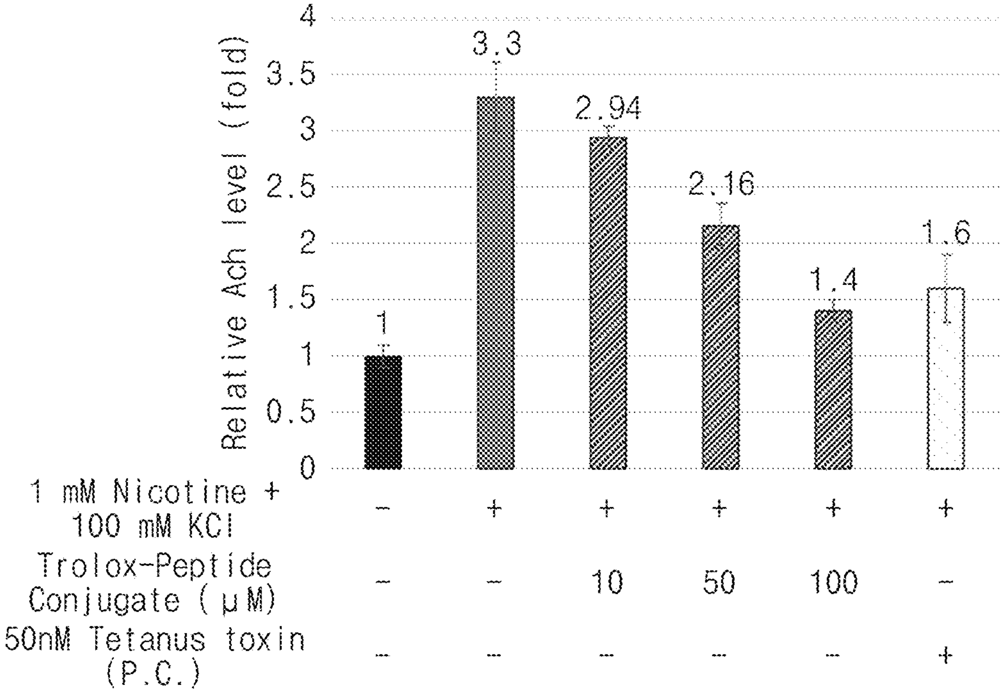
FIG. 1 illustrates an effect of inhibiting the release of a neurotransmitter by treatment with a trolox-peptide conjugate of the present invention in nerve cells: Nicotine and potassium chloride (KCl) are inducing factors for promoting the release of the neurotransmitter; Tetanus is a positive control group.

Hereinafter, the present invention will be described in detail.

One aspect of the present invention provides a peptide comprising an amino acid sequence of SEQ ID NO: 1 and an active substance-peptide conjugate in which an active substance is conjugated to the peptide.

The synthesis of the peptide of the present invention may be performed using, for example, devices or genetic engineering techniques. In the case of synthesis using the devices, a desired peptide may be synthesized using an Fmoc solid-phase method in an automatic peptide synthesizer.

In a specific exemplary embodiment, the peptide including the amino acid sequence of SEQ ID NO: 1 of the present invention was synthesized and identified using the Fmoc solid-phase method, and was selected by verifying the efficacy of the identified peptide.

In a specific exemplary embodiment, in order to verify the efficacy of the identified peptide, peptides for inhibiting the release of the neurotransmitter were selected through validation of a SNARE complex formation inhibitory effect, and a neurotransmitter release inhibitory effect.

Furthermore, the active substance-peptide conjugate of the present invention may be prepared by conjugating the peptide selected through the process with the active substance. In a specific exemplary embodiment, the active substance was selected by verifying the efficacy of the active substance-peptide conjugates prepared by being chemically conjugated with the peptide including the amino acid sequence of SEQ ID NO: 1.

In a specific exemplary embodiment, after 10 types of active substance-peptide conjugates were administered to mice and then conjugates with a DAS analysis result of 4 were first selected, the duration of the muscle relaxation effect was observed, and then at the same dose, the active substance-peptide conjugates showing the longest duration were finally selected.

In the present specification, the term ‘peptide’ refers to a linear molecule consisting of amino acid residues, and specifically, the peptide of the present invention may include the amino acid sequence represented by SEQ ID NO: 1.

The ‘peptide’ may be variants or fragments of amino acids having different sequences by deletion, insertion, substitution or a combination thereof of amino acid residues within the range that does not affect a function. Amino acid exchange that does not entirely alter the activity of the peptide is known in the art. In some cases, the amino acid exchange may be modified by phosphorylation, sulfation, acrylation, glycosylation, methylation, farnesylation, and the like. Accordingly, the present invention includes peptides having an amino acid sequence substantially identical to the peptide having the amino acid sequence of SEQ ID NO: 1, and variants or active fragments thereof. The substantially identical proteins refer to amino acid sequences having at least 75%, preferably at least 80%, for example, at least 85%, at least 90%, at least 95%, at least 98%, or at least 99% of sequence homology with the amino acid sequence of SEQ ID NO: 1, but are not limited thereto, and amino acid sequences having 75% or more homology and the same activity are included in the scope of the present invention. In addition, the peptide of the present invention may further include an amino acid sequence prepared for a specific purpose of increasing a targeting sequence, a tag, labeled residues, and half-life or peptide stability.

In addition, in order to obtain better chemical stability, enhanced pharmacological properties (half-life, absorbency, titer, efficacy, etc.), modified specificity (e.g., a wide biological activity spectrum), and reduced antigenicity, a protective group may bind to an N- or C-terminus of the peptide. For example, the protective group may be an acetyl group, a fluorenylmethoxy carbonyl group, a formyl group, a palmitoyl group, a myristyl group, a stearyl group, or polyethylene glycol (PEG), but may include any ingredient that may enhance the modification of the peptide, particularly the stability of the peptide, without limitation. The ‘stability’ is used to the meaning including not only in-vivo stability that protects the peptide of the present invention from the attack of protein cleavage enzymes in vivo, but also storage stability (e.g., room-temperature storage stability).

As used herein, the term 'active substance' refers to a substance that has at least one carboxyl group, may be chemically conjugated with an N-terminus of the peptide of the present invention, and synergistically induces the activity of the peptide, and specifically, the active substance may be trolox.

The 'trolox' of the present invention is 6-hydroxy-2,5,7,8-tetramethylchroman-2-carboxylic acid, which is a water-soluble analog of vitamin E and is used as an antioxidant. A structure of the trolox is shown in Chemical Formula 1 below.

[Chemical Formula 1]

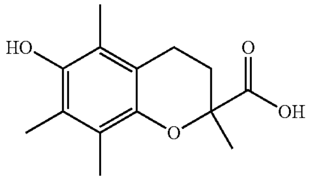

In the active substance-peptide conjugate of the present invention, when the active substance is trolox, the peptide conjugated with trolox was named a "trolox-peptide conjugate".

Specifically, the present invention provides a trolox-peptide conjugate in which trolox is conjugated with a peptide having an amino acid sequence of SEQ ID NO: 1.

The trolox may be conjugated with an N-terminus, C-terminus or side chain of the peptide. Specifically, a carboxyl group of the trolox may be peptide-bound with the N-terminus of the peptide.

An embodiment of the trolox-peptide conjugate may be represented by Chemical Formula 2 below.

conjugate in which a peptide having an amino acid sequence of SEQ ID NO: 1 and trolox are conjugated.

Further, the present invention provides a method for muscle relaxation including administering, to a subject, a trolox-peptide conjugate in which a peptide having an amino acid sequence of SEQ ID NO: 1 and trolox are conjugated.

Further, the present invention provides a trolox-peptide conjugate in which a peptide having an amino acid sequence of SEQ ID NO: 1 and trolox are conjugated, used for muscle relaxation.

Detailed contents of the peptide, the trolox and the trolox-peptide conjugate are as described above.

The trolox-peptide conjugate may relieve muscle contraction or relax muscles by inhibiting the release of the neurotransmitter from the end of the nerve cells.

The composition for muscle relaxation may be prepared in any formulation commonly prepared in the art, and for example, may be formulated and used in the form of oral formulations such as powders, granules, tablets, capsules, suspensions, emulsions, syrups, aerosols, etc., external preparations, suppositories, and sterile injectable solutions according to general methods.

The 'subject' may include humans. In addition, the term 'subject' may be a subject in need of administration of the trolox-peptide conjugate of the present invention, and the subject in need of the administration may be a subject in need of muscle relaxation.

The 'administration' means providing a predetermined substance to a patient by any suitable method, and the administration route of the composition of the present invention may be oral or parenteral administration through all common routes as long as the composition may reach a target tissue. In addition, the composition may be administered by any device capable of moving the active substance to a target cell.

In yet another aspect, the present invention provides a pharmaceutical composition for preventing or treating neuromuscular disorder including the trolox-peptide conjugate as an active ingredient.

[Chemical Formula 2]

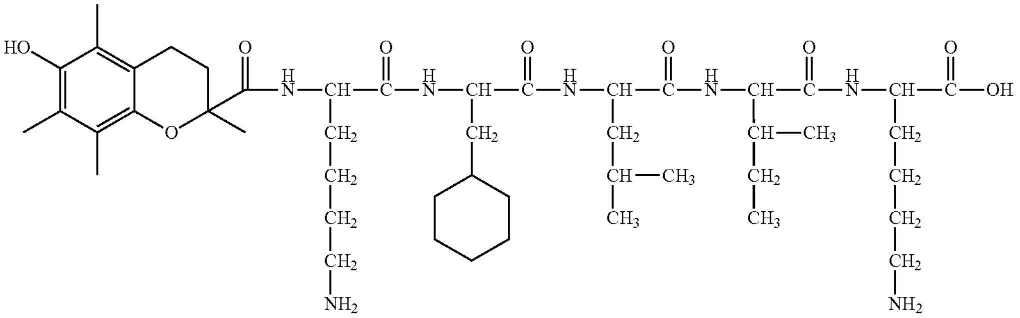

In a specific exemplary embodiment of the present invention, it was confirmed that the trolox-peptide conjugate had an excellent effect of inhibiting the release of the neurotransmitter from the end of nerve cells, and an effect of relaxing contracted muscle in an experimental animal.

In addition, in a specific exemplary embodiment of the present invention, it was confirmed that the trolox-peptide conjugate of the present invention had an excellent effect of relieving muscle contraction and also a remarkable effect of improving skin wrinkles by increasing the expression of proteins constituting the dermis.

In another aspect, the present invention provides a composition for muscle relaxation including a trolox-peptide Further, the present invention provides a method for preventing or treating neuromuscular disorder including administering, to a subject, a trolox-peptide conjugate in which a peptide having an amino acid sequence of SEQ ID NO: 1 and trolox are conjugated.

The subject may be a subject in need of administration of the trolox-peptide conjugate, or may be a subject in need of prevention or treatment of neuromuscular disorder.

Further, the present invention provides a trolox-peptide conjugate in which a peptide having an amino acid sequence of SEQ ID NO: 1 and trolox are conjugated, used for preventing or treating neuromuscular disorder.

The trolox-peptide conjugate may serve to inhibit a neurotransmitter by inhibiting the formation of an SNARE complex, and may be used for preventing or treating neuromuscular disorder for the purpose of relieving muscle contraction or muscle relaxation.

The 'neuromuscular disorder' refers to a disease that may be caused by muscle contraction or stiffness due to excessive release of the neurotransmitter. For example, the neuromuscular disorder may be selected from the group consisting of myoclonus, hemifacial spasm, spasmodic torticollis, anal fissure, blepharospasm, facial spasm, cerebral palsy, strabismus, temporomandibular disorder, neuralgia, myalgia, overactive bladder, urge urinary incontinence, dystonia, hyperhidrosis, and diseases expressed by excessive release of glands controlled by a cholinergic nervous system.

The 'preventing' refers to all actions that suppress or delay the onset of diseases by administering the trolox-peptide conjugate or the composition including the same.

The 'treating' or 'improving' refers to all actions that improve or beneficially change the symptoms of the disease by administration of the trolox-peptide conjugate or the composition including the same.

The composition for preventing or treating the neuromuscular disorder may be formulated and used in the form of oral formulations such as powders, granules, tablets, capsules, suspensions, emulsions, syrups, aerosols, external preparations, suppositories, and sterile injections according to conventional methods, and may include suitable carriers, excipients or diluents commonly used in the preparation of the pharmaceutical composition for formulation.

The pharmaceutically acceptable carrier may include lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, and mineral oil, which are generally used in preparation.

The pharmaceutical composition may further include a lubricant, a wetting agent, a sweetening agent, a flavoring agent, an emulsifying agent, a suspending agent, a preservative, and the like, in addition to the ingredients.

The pharmaceutical composition may be administered orally or parenterally (e.g., applied intramuscularly, intravenously, intraperitoneally, subcutaneously, intradermally, or topically) according to a desired method, and a dose thereof varies depending on the condition and weight of a patient, a degree of disease, a drug form, and route and time of administration, but may be appropriately selected by those skilled in the art.

The pharmaceutical composition is administered in a pharmaceutically effective dose. In the present invention, the 'pharmaceutically effective dose' refers to a sufficient amount to treat the diseases at a reasonable benefit/risk ratio applicable to medical treatment, and an effective dose level may be determined according to factors including the type and severity of disease of a patient, activity of a drug, sensitivity to a drug, a time of administration, a route of administration, an emission rate, duration of treatment, and simultaneously used drugs, and other factors well-known in the medical field. The pharmaceutical composition may be administered as an individual therapeutic agent or in combination with other therapeutic agents, and may be administered simultaneously, separately, or sequentially with conventional therapeutic agents, and may be administered singly or multiply. It is important to administer an amount capable of obtaining a maximum effect with a minimal amount without side effects by considering all the elements, which may be easily determined by those skilled in the art.

The effective dose of the pharmaceutical composition may vary depending on the age, sex, condition, and body weight of a patient, absorbance of an active ingredient in vivo, an inactivation rate, an excretion rate, a disease type, and drugs to be used in combination, and may be increased or decreased according to a route of administration, the severity of obesity, sex, body weight, age, and the like. For example, the pharmaceutical composition may be administered at about 0.0001 μg to 500 mg, preferably 0.01 μg to 100 mg per 1 kg of patient's body weight per day.

In yet another aspect, the present invention provides a composition for improving skin conditions including a trolox-peptide conjugate in which a peptide having an amino acid sequence of SEQ ID NO: 1 and trolox are conjugated, as an active ingredient.

Further, the present invention provides a method for improving skin conditions including administering, to a subject, a trolox-peptide conjugate in which a peptide having an amino acid sequence of SEQ ID NO: 1 and trolox are conjugated.

The subject may be a subject in need of administration of the trolox-peptide conjugate, or a subject in need of improving skin conditions.

Further, the present invention provides a trolox-peptide conjugate in which a peptide having an amino acid sequence of SEQ ID NO: 1 and trolox are conjugated, used for improving skin conditions.

Detailed contents of the peptide, the trolox and the trolox-peptide conjugate are as described above.

The 'skin conditions' refer to a decrease in elasticity of the skin, the formation of wrinkles, or the formation of fine lines on the face caused by skin aging, and the aging includes both endogenous aging and exogenous aging caused by the passage of time, external environment, or the like.

In addition, the wrinkles refer to wrinkles occurring in all body parts including the face, and may include both static rhytides and dynamic rhytides.

The 'improvement of skin conditions' means maintaining or enhancing the ability related to wrinkles and elasticity of the skin, and for example, may be any one selected from the group consisting of reduction of the appearance of fine lines, reduction of the appearance of wrinkles, winding of eyes, lifting the corner of the mouth, reduction of muscle mass, reduction of facial asymmetry, and flattening of the line extending from the upper lip.

The trolox-peptide conjugate inhibits the formation of the SNARE complex to prevent the neurotransmitter from being released, thereby relieving the contraction of the facial muscles and exhibiting an effect of improving skin conditions.

Furthermore, the trolox-peptide conjugate induces i) the increased expression of Col1α1 (collagen type I alpha 1), ii) the increased expression of a fibronectin gene, or iii) the increased expression of an elastin gene to prevent or improve skin wrinkles, thereby exhibiting the effect of improving skin conditions.

Specifically, collagen, a main protein constituting the skin, is synthesized in the form of procollagen in fibroblasts present in the skin dermis and then released into the extracellular matrix, and converted to active collagen, but the trolox-peptide conjugate of the present invention may inhibit the wrinkle formation by increasing the synthesis of the active collagen protein in the skin dermis. In addition, the skin dermis consists of collagen which is collagen fiber and elastin which is elastic fiber. Here, the collagen fiber achieves skin tension formation and structural integration, and the elastin fiber may be involved in skin elasticity to enhance the skin elasticity. Specifically, the trolox-peptide conjugate according to the present invention promotes the expression of elastin, thereby exhibiting an effect of enhancing skin elasticity.

The composition for improving the skin conditions may be a cosmetic composition.

The cosmetic composition may be prepared in any formulation commonly prepared in the art, and may be formulated by, for example, a solution, a suspension, an emulsion, a paste, a gel, a cream, a lotion, a powder, a soap, a surfactant-containing cleansing, oil, a powder foundation, an emulsion foundation, a wax foundation, a spray, and the like, but is not limited thereto.

The cosmetic composition may be prepared in various forms, such as softening lotion, nutrient lotion, nutrient cream, massage cream, essence, eye cream, cleansing cream, cleansing foam, cleansing water, pack, spray, powder, hair tonic, hair cream, hair lotion, hair shampoo, and hair rinse, hair conditioners, hair sprays, hair aerosols, pomades, solutions such as gels, sol gels, emulsions, oils, waxes, aerosols, etc., but is not limited thereto.

The cosmetic composition may include other additives such as excipients and carriers in addition to the trolox-peptide conjugate, and can be applied and mixed with common ingredients mixed in general skin cosmetics as needed.

When the form of the formulation of the cosmetic composition is the paste, cream, or gel, as the carrier ingredient, animal oils, vegetable oils, wax, paraffin, starch, tragacanth, cellulose derivatives, polyethylene glycol, silicone, bentonite, silica, talc, zinc oxide or the like may be used.

When the form of the formulation of the cosmetic composition is the powder or spray, as the carrier ingredient, lactose, talc, silica, aluminum hydroxide, calcium silicate or polyamide powder may be used, and particularly, in the case of the spray, additionally, a propellant such as chlorofluorohydrocarbon, propane/butane or dimethyl ether may be included, but is not limited thereto.

When the form of the formulation of the cosmetic composition is the solution or emulsion, as the carrier ingredient, a solvent, a solubilizing agent or an emulsifying agent may be used. For example, the carrier ingredient may be used with water, ethanol, isopropanol, ethyl carbonate, ethyl acetate, benzyl alcohol, benzyl benzoate, propylene glycol, 1,3-butyl glycol oil, glycerol aliphatic ester, polyethylene glycol or fatty acid ester of sorbitan.

When the form of the formulation of the cosmetic composition is the suspension, as the carrier ingredient, a liquid diluent such as water, ethanol or propylene glycol, a suspension such as ethoxylated isostearyl alcohol, polyoxyethylene sorbitol ester and polyoxyethylene sorbitan ester, microcrystalline cellulose, aluminum metahydroxide, bentonite, agar, tragacanth, or the like may be used.

When the formulation of the cosmetic composition is the surfactant-containing cleansing, as the carrier ingredient, aliphatic alcohol sulfate, aliphatic alcohol ether sulfate, sulfosuccinic acid monoester, isethionate, imidazolinium derivatives, methyltaurate, sarcosinate, fatty acid amide ether sulfate, alkylamido betaine, aliphatic alcohol, fatty acid glyceride, fatty acid diethanolamide, vegetable oil, lanolin derivatives, ethoxylated glycerol fatty acid ester, or the like may be used.

When the formulation of the cosmetic composition is the hair shampoo, base formulation of the cosmetic composition is the hair shampoo, base ingredients for forming the shampoo, such as a thickener, a surfactant, a viscosity modifier, a moisturizer, a pH modifier, a preservative, and essential oil, may be mixed with the trolox-peptide conjugate of the present invention. CDE may be used as the thickener, LES as an anionic surfactant and coco betaine as an amphoteric surfactant may be used as the surfactant, poly quarter may be used as the viscosity modifier, glycerin may be used as the moisturizer, and citric acid and sodium hydroxide may be used as the pH modifier. A grapefruit extract and the like may be used as the preservative, and in addition, essential oils such as cedarwood, peppermint, and rosemary, silk amino acids, pentaol, or vitamin E may be added.

The ingredients included in the cosmetic composition may further include ingredients commonly used in cosmetic compositions, for example, conventional adjuvants such as antioxidants, stabilizers, solubilizers, vitamins, pigments and spices in addition to the trolox-peptide conjugate of the present invention as the active ingredient and the carrier ingredient.

The composition for improving the skin conditions may be a quasi-drug composition.

The 'quasi-drug' refers to products with a milder action than drugs among products used for the purpose of diagnosing, treating, improving, mitigating, treating or preventing human or animal diseases. For example, according to the Pharmaceutical Affairs Act, the quasi-drug includes products used for the treatment or prevention of human/animal diseases, products with mild or no direct action on the human body, etc., by excluding products used for the purpose of drugs.

The quasi-drug composition may be prepared by one or more selected from the group consisting of body cleansers, foams, soaps, masks, ointments, creams, lotions, essences and sprays, but is not limited thereto. In addition, the composition may be prepared in the form of bands, sanitary napkins, etc., but is not limited thereto.

When the trolox-peptide conjugate is used as a quasi-drug additive, the trolox-peptide conjugate may be added as it is or used together with other quasi-drugs or quasi-drug ingredients, and may be appropriately used according to conventional methods.

As described above, the trolox-peptide conjugate of the present invention inhibits the release of the neurotransmitter from the end of nerve cells to have an effect of relieving muscle contraction or relaxing muscles, and thus can be used as a raw material for a drug, a quasi-drug or a cosmetic composition for the purpose of relieving the muscle contraction.

Hereinafter, the present invention will be described in detail by Examples and Experimental Examples.

However, the following Examples and Experimental Examples are just illustrative of the present invention, and the contents of the present invention are not limited to the following Examples and Experimental Examples.

Example 1

Synthesis of Novel Peptide and Confirmation of Physical Properties

1-1. Synthesis of Peptide Including Amino Acid Sequence of SEQ ID NO: 1

A novel peptide sequence 'KFLIK' consisting of an amino acid sequence represented by SEQ ID NO: 1 was prepared using a known method. As a result of measuring the molecular weight of the peptide including the amino acid sequence of SEQ ID NO: 1 using a molecular weight meter, it was confirmed that the molecular weight thereof corresponded to 647.4 Da.

1-2. Evaluation of High-Temperature Stability During Long-Term Storage

The peptide of the present invention consisting of the amino acid sequence of SEQ ID NO: 1 was dissolved in sterile distilled water at a concentration of 1000 ppm, and stored at 45° C. for 7 days, 14 days, 28 days, 60 days, and 75 days, and then HPLC analysis was performed.

As a result, as illustrated in FIG. 1A, it was confirmed that the stability of the peptide of the present invention was maintained under a condition of 45° C. for 75 days, which was a maximum observation day.

1-3. Evaluation of High Temperature Stability

The peptide of the present invention was dissolved in sterile distilled water at a concentration of 1000 ppm, heated at 121° C. for 15 minutes and 30 minutes, and then HPLC analysis was performed.

As a result, as illustrated in FIG. 1B, it was confirmed that the stability of the peptide of the present invention was maintained at 121° C. for 30 minutes, which was a maximum heating time.

Example 2

Preparation of Trolox-Peptide Conjugate

In a peptide reactor, 1 mole of a peptidyl resin and 10 ml of 1-methyl-2-pyrrolidone (NMP) were added, and 270 mg (2.0 equiv.) of 1-hydroxybenzotriazole (1-HOBt) and 759 mg (2.0 equiv.) of N,N,N',N'-tetramethyl-O-(1H-benzotriazol-1-yl) uronium hexafluorophosphate (HBTU) were added and reacted for 30 minutes. Then, the reactant was added with 388 mg (3.0 equiv.) of N, N'-diisopropylethylamine (DIEA) and 500 mg (2.0 equiv.) of trolox, reacted at room temperature for 72 hours, and then filtered. Thereafter, the filtrate and a cleavage solution reacted at room temperature for 2 hours to remove the resin and a protective group. Finally, the filtrate was added with 10 ml of diethyl ether and crystallized to prepare a trolox-peptide conjugate (i.e., a conjugate of a peptide of SEQ ID NO: 1 and trolox). Reaction Formula for preparing the trolox-peptide conjugate was shown in Reaction Formula 1 below.

[Reaction Formula 1]

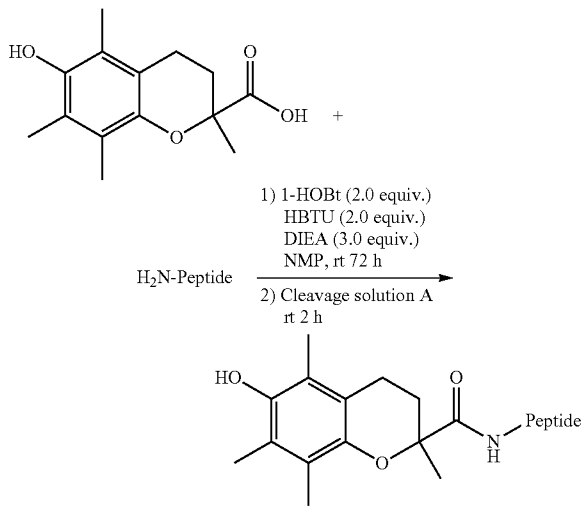

As a result of performing mass spectrometry on the prepared trolox-peptide conjugate, it was confirmed that a trolox-peptide conjugate having a molecular weight of 880.1 Da was synthesized.

Experimental Example 1

Neurotransmitter Release Inhibitory Effect by Trolox-Peptide Conjugate in Nerve Cells In order to confirm a neurotransmitter release inhibitory effect in nerve cells by the trolox-peptide conjugate, the release amount of acetylcholine, which was a neurotransmitter, was measured using a neuroblastoma-derived cell line (SH-SY5Y).

Specifically, SH-SY5Y cells were injected into a dish and cultured for 24 hours in a 37° C., 5% $CO_2$ incubator, and then the medium was replaced with a serum-free medium. Thereafter, the dish was treated with the trolox-peptide conjugate at concentrations of 1 μM, 10 μM, and 50 μM, and as a positive control group, the dish was treated with 50 nM of tetanus and cultured for 48 hours. Thereafter, the release of acetylcholine was induced by treatment with nicotine (NIC) and potassium chloride (KCl) for 30 minutes. Then, the release amount of acetylcholine included in the medium was measured using an acetylcholine assay kit (Abcam).

As a result, as illustrated in FIG. 1, in a group treated with only nicotine (NIC) and potassium chloride (KCl), acetylcholine was released at least three times greater than that in a non-treated control group, but in all groups treated with the trolox-peptide conjugate, the release of acetylcholine was significantly inhibited.

Experimental Example 2

Muscle Relaxation Effect by Trolox-Peptide Conjugate in Experimental Animal 2-1. Preparation of Animal Model Specifically, 7-week-old female Sprague-Dawley rats (Sam Taco BIO KOREA) were used in an animal experiment, and the rats were divided into groups treated with 1 U and 3 U of botulinum neurotoxin (BoNT) and groups treated with 2.5 mg and 5 mg/head of the trolox-peptide conjugate of the present invention, respectively.

The botulinum neurotoxin and the trolox-peptide conjugate of the present invention were administered to the right calf muscle of the experimental animal, respectively.

2-2. Confirmation of Muscle Contraction Relieving Effect

In order to confirm an effect of the trolox-peptide conjugate on muscle relaxation, the time taken for the paralyzed toe muscles to relax for each treated group of Example 2-1 was compared through visual observation analysis.

Specifically, the right foots of the rats administered with each treated group were observed and muscle paralysis was measured using digit abduction scoring (DAS) analysis. In the DAS analysis, mice were floated by their tails for a short period of time to induce a characteristic startle response in the rats, in which the hind limbs were extended and the hind digits were opened. The degree of the startle response in the rats was evaluated with a 5-point scale (0 to 4). Here, Point 0 represented a normal startle response and Point 4 represented maximal reduction in digit abduction and leg extension (Point 0: all five toes were separated; Point 1: one outer toe was attached during abduction; Point 2: three toes were attached; Point 3: four toes were attached; Point 4: all of five toes were attached).

Figure 2:
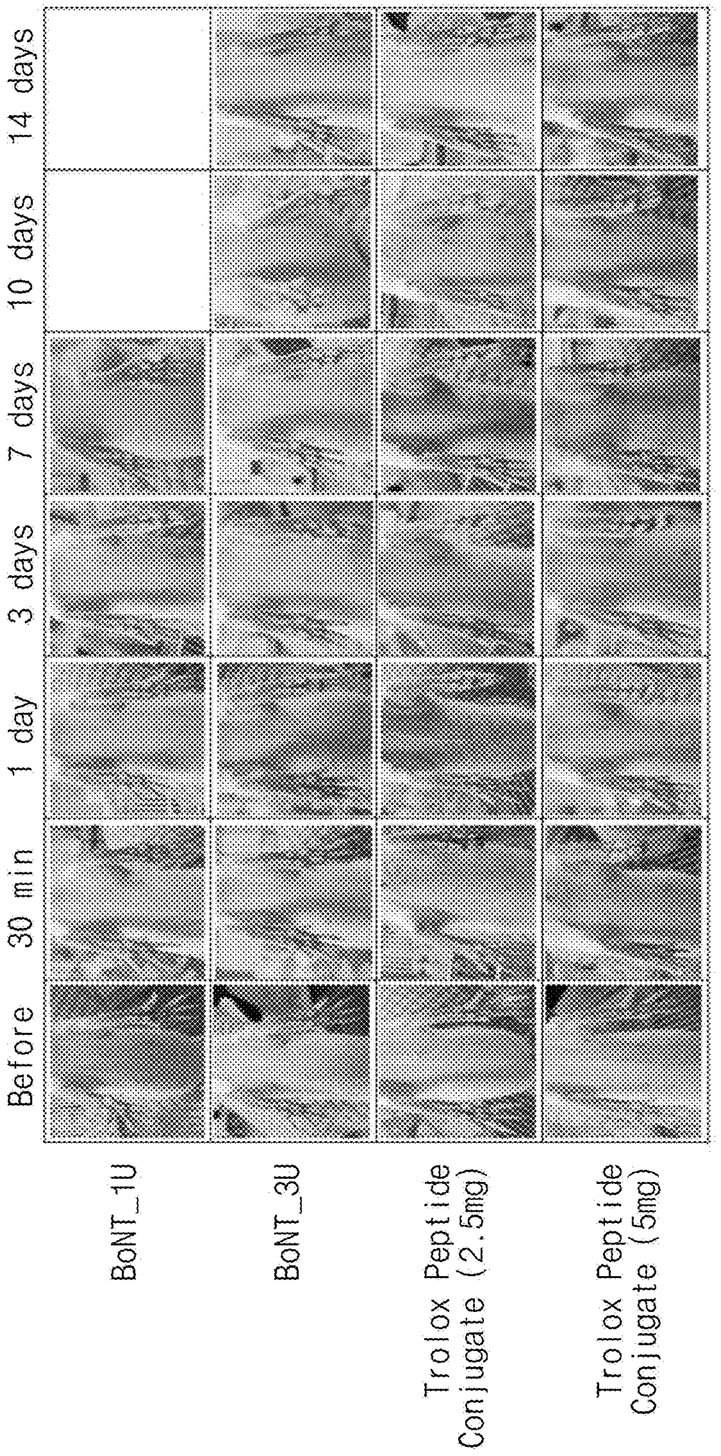
FIG. 2 is a photograph of confirming a muscle relaxation effect by treating an experimental animal with the trolox-peptide conjugate of the present invention; BoNT is a positive control group as botulinum neurotoxin.
Figure 3:
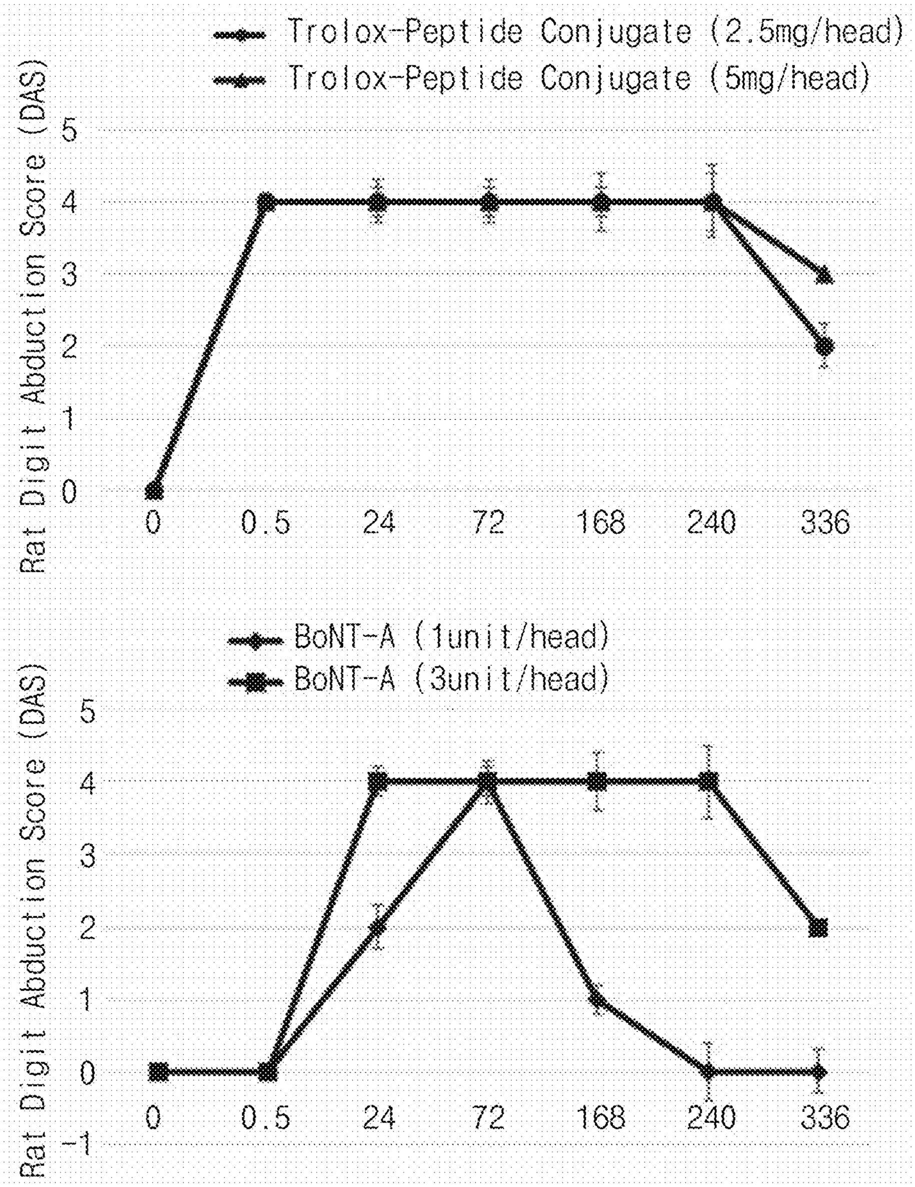
FIG. 3 is a graph of confirming the duration of the muscle relaxation effect by treating an experimental animal with the trolox-peptide conjugate of the present invention: Upper panel illustrates a DAS result when the trolox-peptide conjugate was treated, and lower panel illustrates a DAS result when the botulinum neurotoxin was treated.

As a result, as shown in Table 2 and FIGS. 2 and 3, after 3 days, the muscle relaxation effect was the highest in all groups, and the effect decreased to some extent over time, and the muscle relaxation effect lasted longer in a group injected with the trolox-peptide conjugate of the present invention than in a group injected with Botox.

TABLE 1

| | Score | | | |
|---|---|---|---|---|
| | BoNT/A (Meditoxin) | | SEQ. ID. NO: 1 Conjugate | |
| Time | 1 unit | 3 unit | 2.5 mg | 5 mg |
| 30 min | 0 | 0 | 4 | 4 |
| 1 day | 2 | 4 | 4 | 4 |
| 3 days | 4 | 4 | 4 | 4 |
| 7 days | 1 | 4 | 4 | 4 |
| 10 days | 0 | 4 | 4 | 4 |
| 14 days | 0 | 2 | 2 | 3 |

Experimental Example 3

Effect of Improving Skin Wrinkles by Trolox-Peptide Conjugate

Expression patterns of proteins constituting the dermis were confirmed using mouse fibroblasts (NIH3T3) to confirm whether the trolox-peptide conjugate of the present invention had an effect of improving skin wrinkles.

Specifically, NIH3T3 cells were inoculated into a 6-well plate at a density of $1.5\times10^5$ cells/well and cultured for 16 hours in a 37° C., 5% $CO_2$ incubator. Next, the plate was treated with the trolox-peptide conjugate at concentrations of 1 μM, 10 μM, and 50 μM, cultured again for 16 hours, and then RNA was isolated from the cultured cells. cDNA was synthesized from the isolated RNA using a cDNA synthesis kit (Intron, Korea). The primer base sequences used at this time were as shown in Table 3. The amplified PCR products were subjected to electrophoresis on an agarose gel to confirm DNA bands.

TABLE 2

| Gene | Primer | Base sequence (5'→3') | SEQ ID NO: |
|---|---|---|---|
| collagen type I alpha 1 (Col1a1) | E | CACCCTCAAGA GCCTGAGTC | 2 |
| | R | AGACGGCTGAG TAGGGAACA | 3 |
| Fibronectin | F | CCAGGAACCGA GTACACCAT | 4 |
| | R | ATACCCAGGTT GGGTGATGA | 5 |
| Elastin | F | GGACCCCTGAC TCGCGACCT | 6 |
| | R | GGGGAGGTGGG ACTGCCCAA | 7 |
| Glyceraldehyde 3-phosphate dehydrogenase (GAPDH) | F | GGTGTGAACGGAT TTGGCCGTATTG | 8 |
| | R | CCGTTGAATTTGC CGTGAGTGGAGT | 9 |

Figure 4:
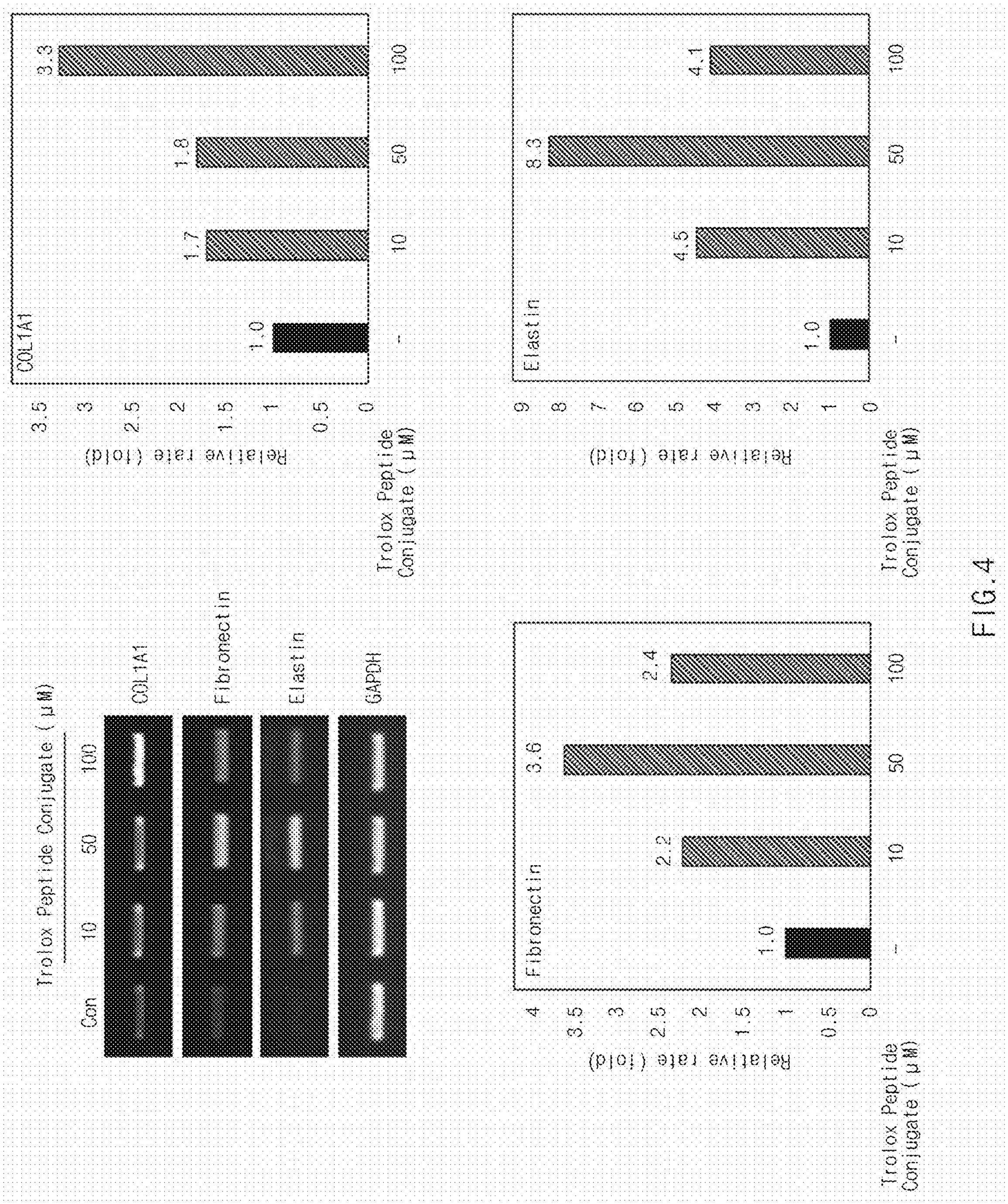
FIG. 4 illustrates an effect of increasing the expression of COL1A1, fibronectin, and elastin constituting the dermis by the trolox-peptide conjugate of the present invention in fibroblasts.

As a result, as illustrated in FIG. 4, it was confirmed that the expression levels of collagen, fibronectin, and elastin were significantly increased when the trolox-peptide conjugate was treated compared to a control group.

As a result, it can be seen that the trolox-peptide conjugate can exhibit an effect of preventing or improving skin wrinkles by increasing the expression levels of the proteins constituting the dermis.

The invention claimed is:

1. A trolox-peptide conjugate in which a peptide having an amino acid sequence of SEQ ID NO: 1 and trolox are conjugated, wherein a carboxyl group of the trolox is peptide-bound with an N-terminus of the peptide.

2. A method for muscle relaxation in a subject in need thereof comprising administering an effective amount of the trolox-peptide conjugate according to claim 1 to the subject.

3. The method for muscle relaxation of claim 2, wherein the trolox-peptide conjugate relieves muscle contraction by inhibiting a release of a neurotransmitter.

4. A method for treating a neuromuscular disorder in a subject in need thereof comprising administering an effective amount of the trolox-peptide conjugate according to claim 1 to the subject.

5. The method for treating neuromuscular disorder of claim 4, wherein the neuromuscular disorder is selected from the group consisting of myoclonus, hemifacial spasm, spasmodic torticollis, anal fissure, blepharospasm, facial spasm, cerebral palsy, strabismus, temporomandibular disorder, neuralgia, myalgia, overactive bladder, urge urinary incontinence, dystonia, and hyperhidrosis.

6. A method for improving a skin condition in a subject in need thereof comprising administering an effective amount of the trolox-peptide conjugate according to claim 1 to the subject, wherein the skin condition improved by the trolox-peptide conjugate is selected from the group consisting of reduction of an appearance of fine lines, reduction of an appearance of wrinkles, widening of the eyes, lifting a corner of the mouth of the subject, reduction of muscle mass, reduction of facial asymmetry, and flattening of a line extending from the upper lip of the subject, and wherein the trolox-peptide conjugate improves wrinkles by i) increasing an expression of ColIα1 (collagen type I alpha 1), ii) increasing an expression of a fibronectin gene, or iii) increasing an expression of an elastin gene.

7. The method for improving a skin condition of claim 6, wherein the trolox-peptide conjugate relieves contraction of facial muscles by inhibiting a release of a neurotransmitter.

* * * * *